United States Patent [19]
Myello et al.

[11] Patent Number: 5,865,820
[45] Date of Patent: Feb. 2, 1999

[54] WATER RESISTANT PROTECTION SEALING APPARATUS FOR ILEOSTOMY OR UROSTOMY APPLIANCE

[76] Inventors: Peter J. Myello, deceased, late of Penninsula, Ohio; by Judith Kloss, executrix, 2034 Stine Rd., Penninsula, Ohio 44264

[21] Appl. No.: 835,392

[22] Filed: Apr. 7, 1997

[51] Int. Cl.[6] ..................................................... A61F 5/44
[52] U.S. Cl. ........................ 604/345; 604/337; 2/312
[58] Field of Search ................................. 604/327, 332, 604/337, 338, 339, 341, 342, 345; 2/311, 312, 318, 319

[56] References Cited

U.S. PATENT DOCUMENTS

| | | |
|---|---|---|
| 2,656,838 | 10/1953 | McConnell ............................ 128/283 |
| 2,675,002 | 4/1954 | Cesare . |
| 3,302,647 | 2/1967 | Marsan . |
| 3,398,744 | 8/1968 | Hooper . |
| 4,636,206 | 1/1987 | Ederati et al. . |
| 4,714,465 | 12/1987 | Steer . |
| 5,178,614 | 1/1993 | McDowell et al. . |

*Primary Examiner*—John G. Weiss
*Assistant Examiner*—Dennis Ruhl

[57] ABSTRACT

A device to be worn by wearers of ileostomy, urostomy or the like appliances in areas where high levels of moisture is present. The semi-pliable, moisture/water-proof, protective device is most appropriately used when showering or for similar water-present activities. The device is non-invasive and allows for the unadulterated use of the wearer's present appliance without transforming the existing pouch, but with the device's inclusion which encompasses a belt apparatus, sealing ring structure and fastening means.

8 Claims, 7 Drawing Sheets

WATER RESISTANT PROTECTION SEALING APPARATUS FOR ILEOSTOMY OR UROSTOMY APPLIANCE

BACKGROUND OF THE INVENTION

1. Field of the Invention

The present invention relates generally to protective sealing apparatus and, more particularly, to a water resistant sealing apparatus for protection of ileostomy appliances, urostomy appliances, and the like.

2. Description of the Related Art

As is well-known in the art, ileostomy appliances, urostomy appliances, colostomy appliance, etc. are widely known and used as a prosthetic utilized following various surgical procedures. Examples of such appliances appear in the prior art, for example, in U.S. Pat. No. 3,398,774, issued in the name of Hooper et al., in U.S. Pat. No. 2,675,002, issued in the name of Desare, in U.S. Pat. No. 2,656,838, issued in the name of McConnell, and in U.S. Pat. No. 3,713,445, issued in the name of Marsan.

Those faced with regular, extended usage of such appliances continually encounter a problem in keeping these appliances dry: if the appliance gets wet, its adhesive becomes ineffective, causing the bag to no longer adhere to the skin of the wearer. When this occurs, the appliance must be discarded and replaced.

Numerous attempts exist in the related arts for protection of such or similar appliances. For instance, U.S. Pat. No. 5,178,614, issued in the name of McDowell et al., discloses a protective shield for a stoma pouch. However, the protective shield therein described requires the use of a face plate flange (35), and a shield having a rigid thin shell (50) such as to cause the device to be restrictive and bulky enough to be ineffective with urostomy and colostomy appliances.

Another example of a urostomy guard is disclosed in U.S. Pat. No. 4,636,206, issued in the name of Ederati et al. However, such a urostomy guard as disclosed in the Ederati et al. invention fails to provide a lightweight, watertight seal that is easily adaptable to fit a variety of people. Consequently, a need has been felt for providing such an apparatus.

SUMMARY OF THE INVENTION

It is therefore an object of the present invention to provide an improved protective sealing apparatus for providing a water resistant seal for aqueous protection of ileostomy appliances, urostomy appliances, and the like.

It is a feature of the present invention to provide an improved water resistant protection sealing apparatus for an ileostomy or urostomy appliance having a lightweight, watertight plastic cap, capable of being manufactured in an economical manner.

It is another feature of the present invention to provide an improved water resistant protection sealing apparatus for an Ileostomy or urostomy appliance having a waterproof seal fitting against the body of the wearer for preventing aqueous intrusion into the appliance during activities such as showering, bathing, swimming, etc.

It is yet another feature of the present invention to provide an improved water resistant protection sealing apparatus for an ileostomy or urostomy appliance having an elastic belt supporting means for expandably fitting around a wearer, and further having a hook and loop fastening means such as VELCRO for easily securing and removing the belt.

Finally, the present invention provides the above features in a compact, comfortable design which reduces the limitations on the mobility of the wearer.

Briefly described according to the preferred embodiment of the present invention, an appliance bag cover assembly is provided supported by an elastic support means comprising a ⅛" thick elastic belt which is approximately 6 inches wide at its widest point and 4 inches wide at its narrowest point, and secured via a hook and loop fastener means such as VELCRO. A plastic cap has a diameter of 5 inches at its top and 6 inches at its base. From top to bottom, the cap is one inch in height.

To use the present invention, a wearer must first empty the colostomy or urostomy pouch, and then reattach and close it. Next, the user grasps the plastic cap in one hand and the elastic belt in the other, and places the cap's smaller diameter into the five-inch hole in the belt. The pouch is then folded and placed into the plastic cap. By positioning the cap over the colostomy or urostomy, the user can then seal the area while affixing the belt support means around the wearer's body. The tension of the elastic securely maintains the cap over the urostomy or colostomy; the single waterproof seal provides a watertight barrier during bathing, showering, swimming, or other water-borne activity. While the seal is maintained, the user is free to temporarily engage in various activities which would otherwise result in the need to replace the pouch.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

1. Detailed Description of the Figures

Figure 1:
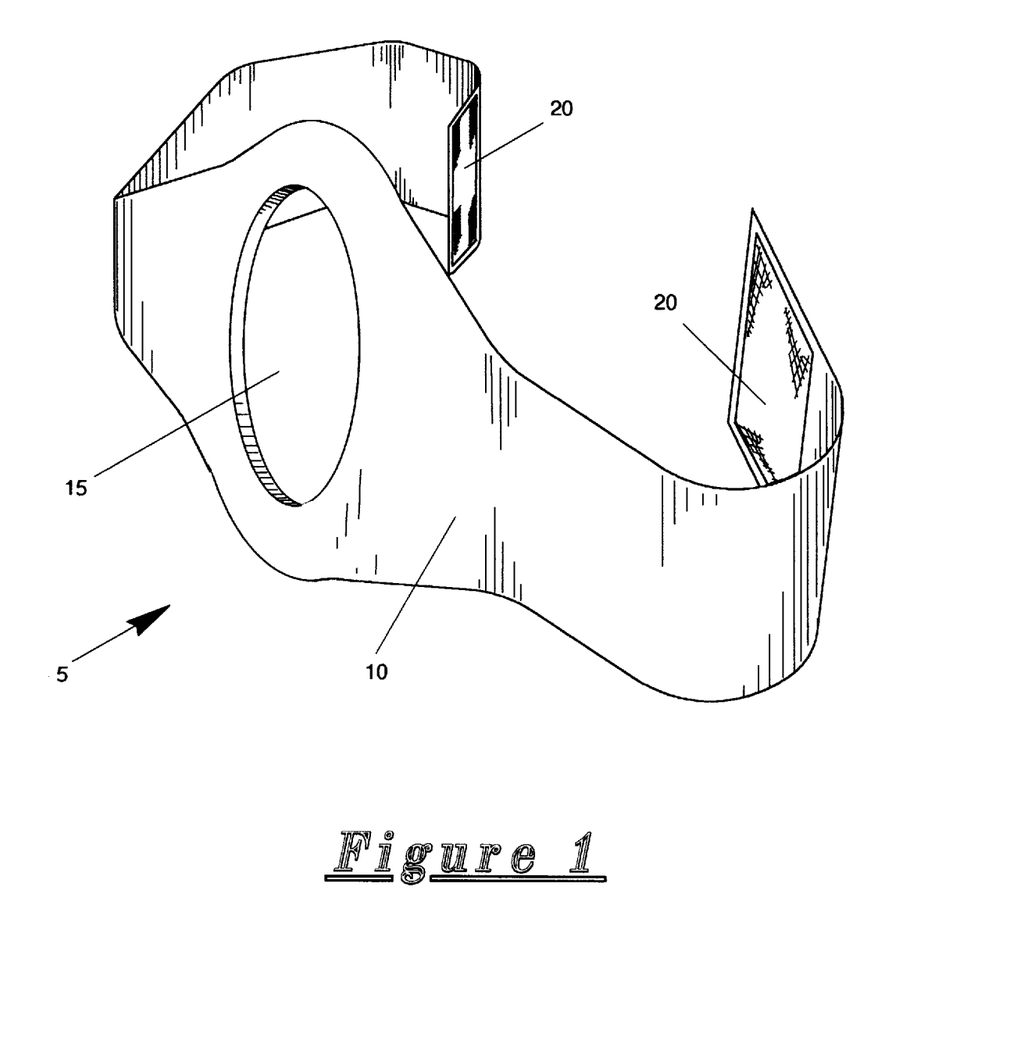
FIG. 1 is a perspective view of the preferred embodiment of the elastic support means for use with a water resistant protection sealing apparatus for ileostomy or urostomy appliances according to the present invention.

Referring now to FIG. 1, a water resistant protection sealing apparatus for ileostomy or urostomy appliance 5 is shown in partial form, according to the present invention, in which the elastic support means 10 is depicted. The elastic support means 10 is composed of one solid, continuous piece of material and is of an elastic nature. It is envisioned that the elastic support means 10 would be comprised of a neoprene rubber material, though it can be easily seen by those familiar in the art that other flexible, elastic and waterproof materials could be substituted. The overall width of the elastic support means 10 is approximately 6 inches at the widest point at the middle of the elastic support means 10 and taper in a linear fashion to approximately 4 inches at each of the opposing ends. The overall length of the elastic support means 10 would be directly related to the circumference of the user's body and would be approximately 6 inches longer than the circumference of the user's body. Finally, the thickness of the elastic support means 10 would be approximately one-eighth of an inch thick. Located at the midpoint of the lengthwise dimension is a round opening 15. The diameter of the elastic support means 10 is approximately 5 inches. Within the round opening 15 is placed other components of the water resistant protection sealing apparatus for ileostomy or urostomy appliance 5 which will be described in greater detail in following figures. Located at each opposing end of the elastic support means 10 in the lengthwise dimension is a hook and loop fastening means 20. It is envisioned that the hook and loop fastening means 20 would be a material such as VELCRO, though other materials or fastening means could be utilized with equal results.

Figure 2:
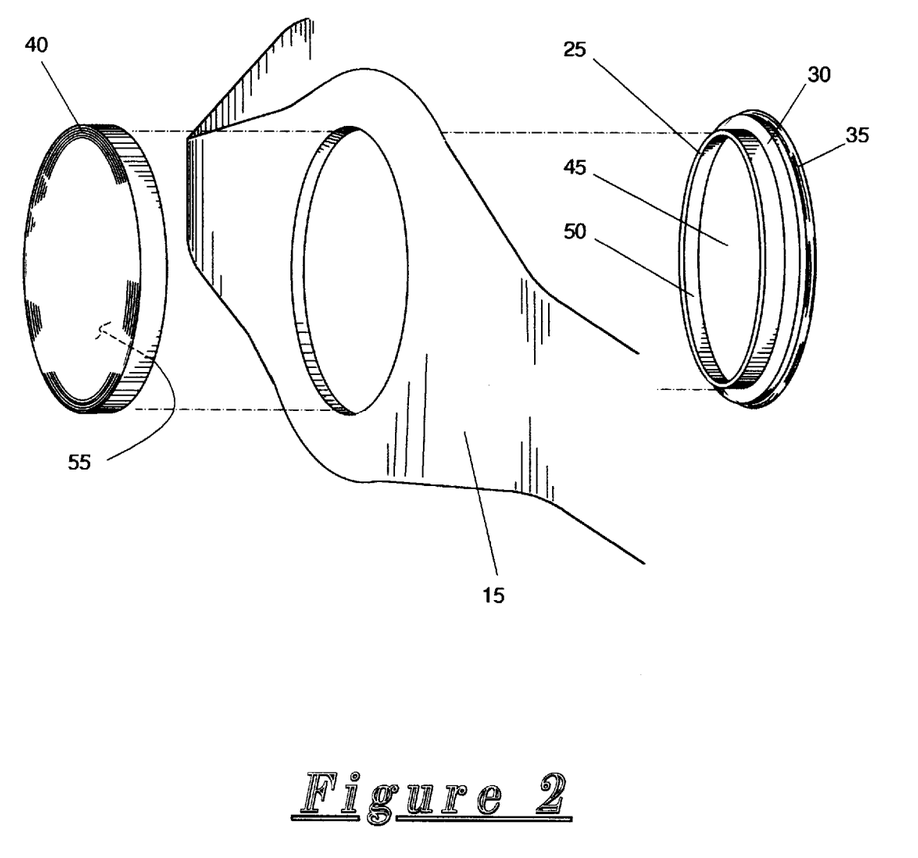
FIG. 2 is an exploded perspective view of a water resistant protection sealing apparatus for ileostomy or urostomy appliances according to the present invention.

Referring next to FIG. 2, an exploded perspective view of the water resistant protection sealing apparatus for ileostomy or urostomy appliance 5 is shown according to the present invention. A sealing ring 25 is placed into the round opening 15 of the elastic support means 10. The extension of the sealing ring 25 is continued until a shoulder surface 30 comes in contact with and is seated against the back surface of the elastic support means 10. The sealing ring 25 would be manufactured from plastic as to allow a rigid, waterproof structure that would be easily manufactured by traditional plastic injection molding techniques in a cost effective manner. The sealing ring 25 has an approximate overall diameter of six inches, with a diameter of five inches not including the shoulder surface 30. The overall height of the sealing ring 25 is approximately 1 inch. Around the outermost circumference of the sealing ring 25 is a cylindrical sealing means 35 such as a rubber O-ring. The functions of the cylindrical sealing means 35 along with other pertinent data on the sealing ring 25 will be described in greater detail in following figures. After the sealing ring 25 is placed into the round opening 15 of the elastic support means 10, a protective cap 40 is then snapped onto the outward facing rim of the sealing ring 25. The protective cap 40 would be manufactured from plastic as to allow a rigid, waterproof structure that would be easily manufactured by traditional plastic injection molding techniques in a cost effective manner. A cylindrical cavity 45 is now defined by a wall surface of the sealing ring 50, by an interior surface of the protective cap 55, and the user's body (not shown in this FIG.). It is in this cylindrical cavity 45 that the ileostomy or urostomy bag (provided by the user and not shown in this FIG) would be placed.

Figure 3:
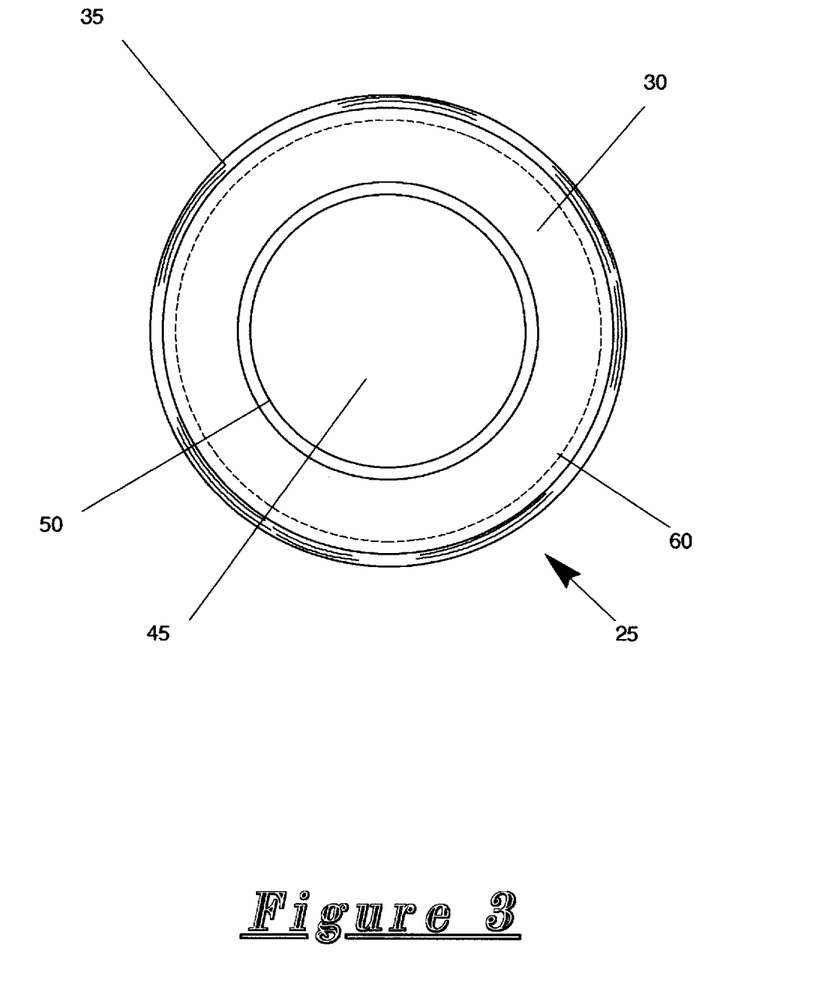
FIG. 3 is a top plan view of a sealing ring for use therewith.

Referring now to FIG. 3, a top plan view of the sealing ring 25 is disclosed. A cylindrical tapered edge 60 conforms to and provides the transition between the shoulder surface 30 and the cylindrical sealing means 35. The angle formed by the cylindrical tapered edge 60 is approximately 45 degrees and thus provides a degree of protection against any sharp edges for the wearer. The wall surface of the sealing ring 50 can also be more easily visualized providing the cylindrical cavity 45.

Figure 4:
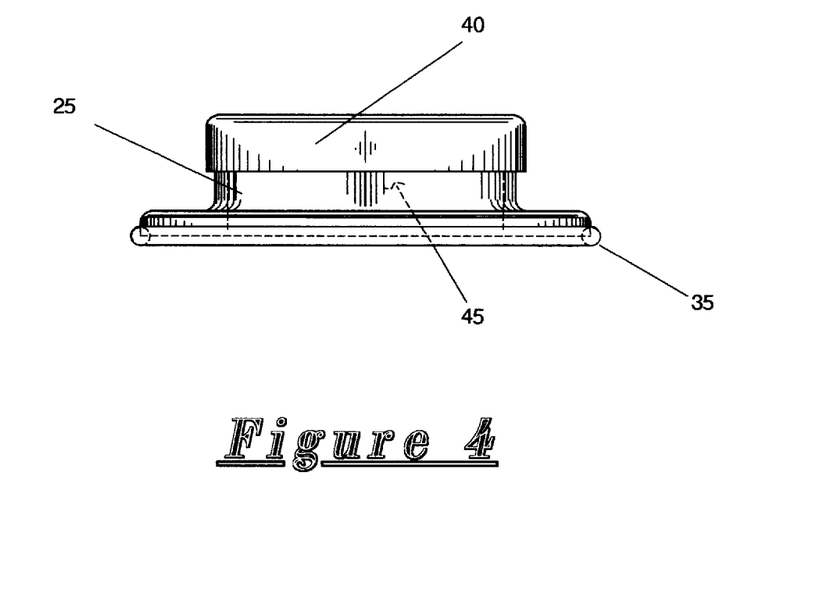
FIG. 4 is a side elevational view thereof shown with cap in place.

Referring next to FIG. 4, a side elevational view of the sealing ring 25 with the protective cap 40 in a closed condition is disclosed. It is in this closed condition that the wearer would be allowed entry into an aqueous environment while allowing the ileostomy or urostomy bag (not shown in this FIG.) stored within the cylindrical cavity 45 to remain in a dry condition. To gain entry into the cylindrical cavity 45 after vacating the aqueous environment, the wearer could simply release the elastic support means 10 (as shown in FIG. 2) or if the wearer intends to reenter the aqueous environment in the immediate future, the wearer could remove the protective cap 40 from the sealing ring 25 thus enabling the cylindrical sealing means 35 to maintain contact with the wearer's skin surface.

Figure 5:
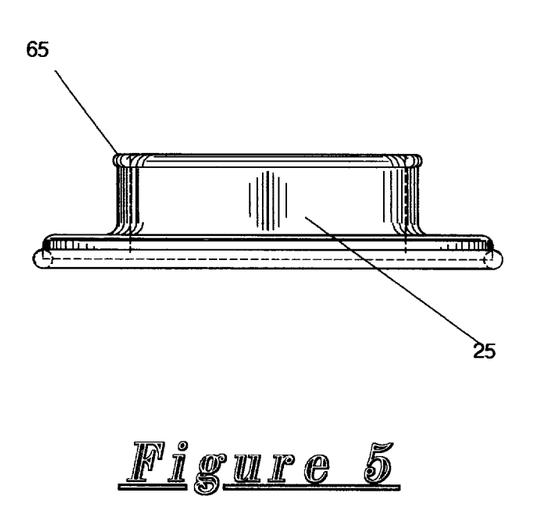
FIG. 5 is a side elevational view thereof shown alone.

Referring now to FIG. 5, a side elevational view of the sealing ring 25 is shown alone. A ridged rim 65 is provided to allow firm mechanical contact with the protective cap 40 (as shown in FIG. 4). The ridged rim 65 is continuous around the entire circumference of the upper edge of the sealing ring 25 and provides an extrusion dimension such that the protective cap 40 (as shown in FIG. 4) cannot be easily displaced or removed without considerable and purposeful force.

Figure 6:
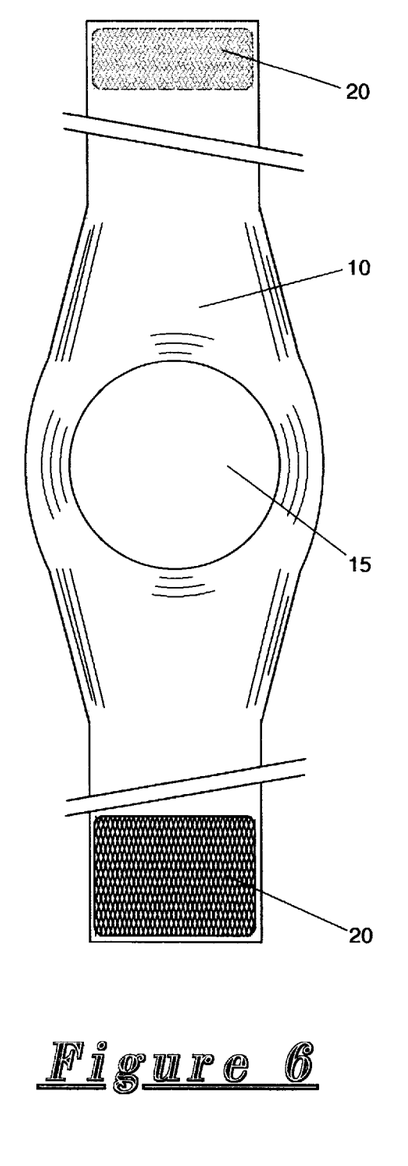
FIG. 6 is a top plan view of the elastic support means depicted in FIG. 1.

Referring next to FIG. 6, a top plan view of the elastic support means 10 is depicted. The hook and loop fastening means 20, when connected together in a closed state allows the elastic support means 10 to form an irregular but closed loop around the wearer's body. The elastic properties of the elastic support means 10 throughout its entire length allow for an equally distributed force in an inward direction toward the interior of the formed loop. This force in the area of the round opening 15 is what allows the cylindrical sealing means 35 on the sealing ring 25 to maintain its water tight seal against the wearer's body. (not shown in this FIG.)

Figure 7:
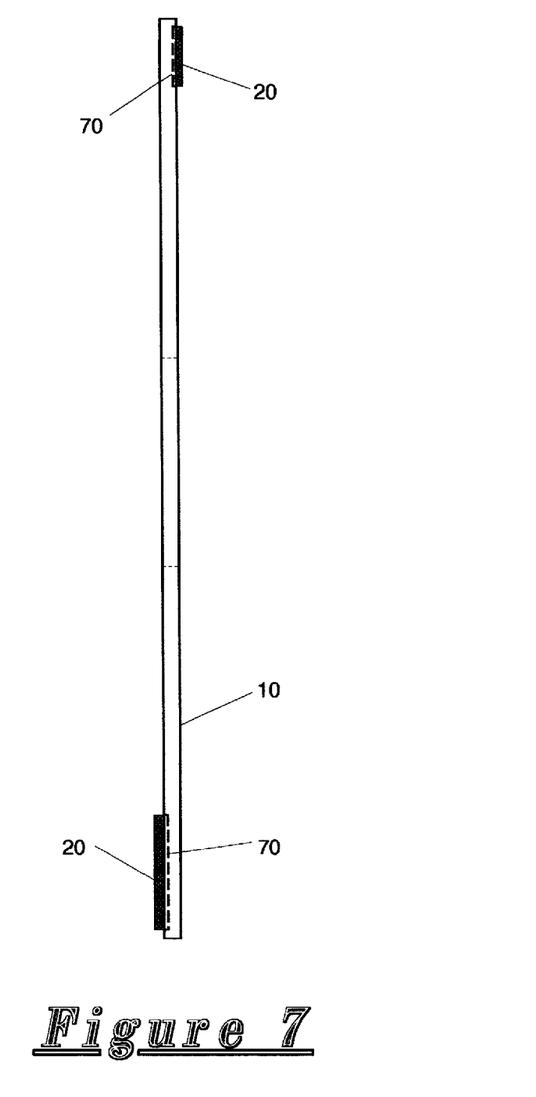
FIG. 7 is a side elevational view thereof.

Referring finally to FIG. 7, a side elevational view of the elastic support means 10 is disclosed. The hook and loop fastening means 20 is held in firm mechanical contact with the elastic support means 10 via a fastening means 70, for connecting two flexible materials together. It is envisioned that the fastening means 70 could be of the chemical adhesive variety, although thread based stitching would equally suffice.

2. Operation of the Preferred Embodiment

In operation, the present invention can be installed and utilized by the common user suffering from the confinement of an ileostomy or urostomy appliance in a simple and effortless manner. To use the present invention with its preferred embodiment can best be described in conjunction with the perspective view of FIG. 1 and the exploded perspective view of FIG. 2 depicting the water resistant protection sealing apparatus for ileostomy or urostomy appliance 5.

Before entering the aqueous environment, the wearer would first empty the colostomy or urostomy pouch, then reattach it and close it in the conventional manner. Next, the wearer would grasp the sealing ring 25 in one hand and the elastic support means 10 in the other. By placing the surface of the sealing ring 25 with the cylindrical tapered edge 60 through the round opening 15 of the elastic support means 10, until the shoulder surface 30 makes physical contact with the elastic support means 10, and placing the cylindrical sealing means 35 up against his or her body around the colostomy or urostomy pouch, two-thirds of the necessary surfaces required to define the cylindrical cavity 45 are present. Next, the elastic support means 10 is secured around the wearer's body by use of the hook and loop fastening means 20. Next, the urostomy or colostomy pouch is folded and placed inside the cylindrical cavity 45 and the protective cap 40 is attached the sealing ring 25 via means of the ridged rim 65. At this point, the interior surface of the protective cap 55 has defined the last remaining surface of the cylindrical cavity 45 and the wearer is now ready to enter the aqueous environment for a limited time for bathing, showering, or swimming purposes.

After completion of the duties required in the aqueous environment, the wearer would dry his or her body around the area of the water resistant protection sealing apparatus for ileostomy or urostomy appliance 5 using a towel or other conventional manner. Access to the colostomy or urostomy pouch could then be gained via removal of just the protective cap 40 or via removal of the entire water resistant protection sealing apparatus for ileostomy or urostomy appliance 5 by separating the hook and loop fastening means 20, removing the elastic support means 10 and thus the sealing ring 25 and protective cap 40.

The foregoing description is included to illustrate the operation of the preferred embodiment and is not meant to limit the scope of the invention. The scope of the invention is to be limited only by the following claims.

What is claimed is:

1. A water resistant protection sealing apparatus for ileostomy or urostomy appliance comprising:

elastic support means, said elastic support means being generally elongated and forming a round opening located at a midpoint of a lengthwise dimension, a sealing ring, said sealing ring placed within said round opening of said elastic support means, said sealing ring having a lateral extension protruding from a shoulder surface, wherein said lateral extension inserts through said round opening in such a manner that said shoulder surface comes in contact with and is seated against the back surface of said elastic support means;

cylindrical sealing means for surrounding the outermost circumference of said sealing ring;

a protective cap for snapping onto said lateral extension protrusion of the sealing ring after said sealing ring is placed into the round opening of said elastic support means;

and wherein a cylindrical cavity is thereby defined by a wall surface of the sealing ring, by an interior surface of the protective cap, and the user's body when the device is worn, such that in this cylindrical cavity the ileostomy or urostomy appliance can be placed.

2. The water resistant protection sealing apparatus for ileostomy or urostomy appliance as described in claim 1, wherein said elastic support means is composed of one solid, continuous piece of material which is elastic nature.

3. The water resistant protection sealing apparatus for ileostomy or urostomy appliance as described in claim 2, wherein said elastic support means is comprised of a neoprene rubber material.

4. The water resistant protection sealing apparatus for ileostomy or urostomy appliance as described in claim 1, wherein said elastic support means is approximately six inches at the widest point at said midpoint of the elastic support means and tapers to approximately 4 inches.

5. The water resistant protection sealing apparatus for ileostomy or urostomy appliance as described in claim 1, further comprising:

hook and loop fastening means located at each opposing end of the elastic support means.

6. The water resistant protection sealing apparatus for ileostomy or urostomy appliance as described in claim 1, wherein said sealing ring is manufactured from plastic as to allow a rigid, waterproof structure that would be easily manufactured by traditional plastic injection molding techniques.

7. The water resistant protection sealing apparatus for ileostomy or urostomy appliance as described in claim 6, wherein said sealing ring has an approximate overall diameter of six inches, with a diameter of five inches not including said shoulder surface.

8. The water resistant protection sealing apparatus for ileostomy or urostomy appliance as described in claim 1, wherein said sealing ring includes a cylindrical tapered edge for conforming to and providing a transition between the shoulder surface and the cylindrical sealing means.

* * * * *